United States Patent
Michelson

(10) Patent No.: US 7,063,701 B2
(45) Date of Patent: Jun. 20, 2006

(54) SCREWS OF CORTICAL BONE HAVING A TRAILING END CONFIGURED TO COOPERATIVELY ENGAGE AN IMPLANT

(75) Inventor: Gary K. Michelson, Venice, CA (US)

(73) Assignee: SDGI Holdings, Inc., Wilmington, DE (US)

( * ) Notice: Subject to any disclaimer, the term of this patent is extended or adjusted under 35 U.S.C. 154(b) by 109 days.

(21) Appl. No.: 09/970,241

(22) Filed: Oct. 2, 2001

(65) Prior Publication Data
US 2002/0022843 A1    Feb. 21, 2002

Related U.S. Application Data

(62) Division of application No. 09/566,055, filed on May 5, 2000.

(60) Provisional application No. 60/132,671, filed on May 5, 1999.

(51) Int. Cl.
*A61B 17/86* (2006.01)

(52) U.S. Cl. ............... 606/73; 606/70; 606/76; 606/77; 606/61

(58) Field of Classification Search ........... 606/62–73, 606/61, 76, 77; 623/16.11, 17.11, 23.51, 623/23.58, 23.61, 26.63; 411/411, 417, 423, 411/416, 308, 904
See application file for complete search history.

(56) References Cited

U.S. PATENT DOCUMENTS

| | | | |
|---|---|---|---|
| 4,537,185 A | 8/1985 | Stednitz | |
| 4,794,918 A | 1/1989 | Wolter | |
| 5,013,316 A | 5/1991 | Goble et al. | |
| 5,053,036 A | 10/1991 | Perren et al. | |
| 5,084,050 A | 1/1992 | Draenert | |
| 5,088,869 A * | 2/1992 | Greenslade | 411/386 |
| 5,108,399 A | 4/1992 | Eitenmuller et al. | |
| 5,129,906 A | 7/1992 | Ross et al. | |
| 5,167,664 A | 12/1992 | Hodorek | |
| 5,169,400 A | 12/1992 | Mulhing et al. | |
| 5,201,733 A | 4/1993 | Etheredge, III | |
| 5,217,462 A | 6/1993 | Asnis et al. | |
| 5,275,601 A * | 1/1994 | Gogolewski et al. | 606/73 |
| 5,360,448 A | 11/1994 | Thramann | |
| 5,360,450 A | 11/1994 | Giannini | |
| 5,364,400 A | 11/1994 | Rego, Jr. et al. | |
| 5,417,533 A | 5/1995 | Lasner | |
| 5,439,684 A | 8/1995 | Prewett et al. | |
| 5,470,334 A | 11/1995 | Ross et al. | |
| 5,584,836 A | 12/1996 | Ballintyn et al. | |
| 5,601,553 A * | 2/1997 | Trebing et al. | 606/61 |
| 5,868,749 A | 2/1999 | Reed | |

(Continued)

*Primary Examiner*—David O. Reip
(74) *Attorney, Agent, or Firm*—Martin & Ferraro, LLP

(57) ABSTRACT

A screw formed of cortical bone for use in the human body with an implant having a screw hole for receiving at least a portion of a screw therethrough, includes a shaft with a thread along at least a portion of its length. The thread has an outer diameter dimensioned to pass through the screw hole in the implant. The trailing end of the screw is configured to cooperatively engage at least a portion of the screw hole of the implant so as to prevent the screw from linear motion along the mid-longitudinal axis of the shaft in a direction opposite to the direction of insertion when the screw is threaded through the screw hole to attach the implant to a bone portion of the human body. The screw is formed substantially of cortical bone of a single cortical thickness.

73 Claims, 10 Drawing Sheets

U.S. PATENT DOCUMENTS

| | | |
|---|---|---|
| 5,895,426 A | 4/1999 | Scarborough et al. |
| 5,904,683 A | 5/1999 | Pohndorf et al. |
| 5,904,710 A | 5/1999 | Errico et al. |
| 5,968,047 A | 10/1999 | Reed |
| 5,989,289 A | 11/1999 | Coates et al. |
| 6,030,162 A * | 2/2000 | Huebner ............... 411/413 |
| 6,033,438 A | 3/2000 | Bianchi et al. |
| 6,045,554 A | 4/2000 | Grooms et al. |
| 6,045,580 A | 4/2000 | Scarborough et al. |
| 6,048,204 A * | 4/2000 | Klardie et al. ........... 433/174 |
| 6,048,344 A * | 4/2000 | Schenk ................. 606/73 |
| 6,099,529 A | 8/2000 | Gertzman et al. |
| 6,123,731 A | 9/2000 | Boyce et al. |
| 6,129,730 A * | 10/2000 | Bono et al. ............. 606/73 |
| 6,139,550 A | 10/2000 | Michelson |
| 6,152,927 A | 11/2000 | Farris et al. |
| 6,162,225 A | 12/2000 | Gertzman et al. |
| 6,193,721 B1 | 2/2001 | Michelson |
| 6,200,347 B1 | 3/2001 | Anderson et al. |
| 6,206,922 B1 | 3/2001 | Zdeblick et al. |
| 6,206,923 B1 | 3/2001 | Boyd et al. |
| 6,224,602 B1 | 5/2001 | Hayes |
| 6,235,033 B1 | 5/2001 | Brace et al. |
| 6,235,034 B1 | 5/2001 | Bray |
| 6,248,108 B1 * | 6/2001 | Tormala et al. ............ 606/73 |
| 6,258,125 B1 | 7/2001 | Paul et al. |
| 6,270,528 B1 | 8/2001 | McKay |
| 6,620,163 B1 | 9/2003 | Michelson |

* cited by examiner

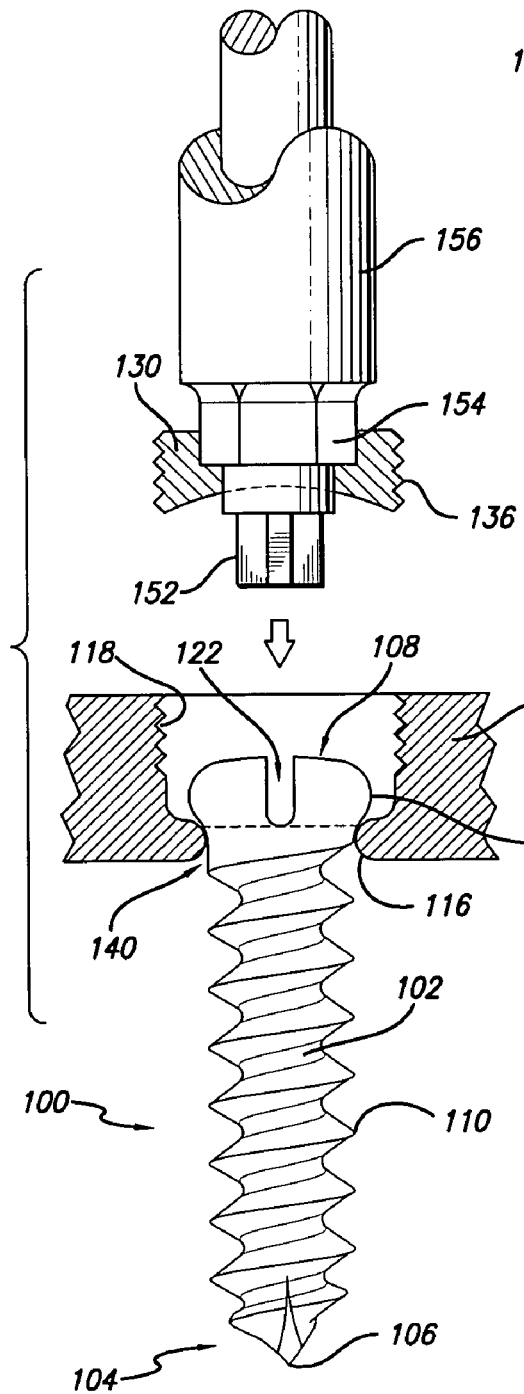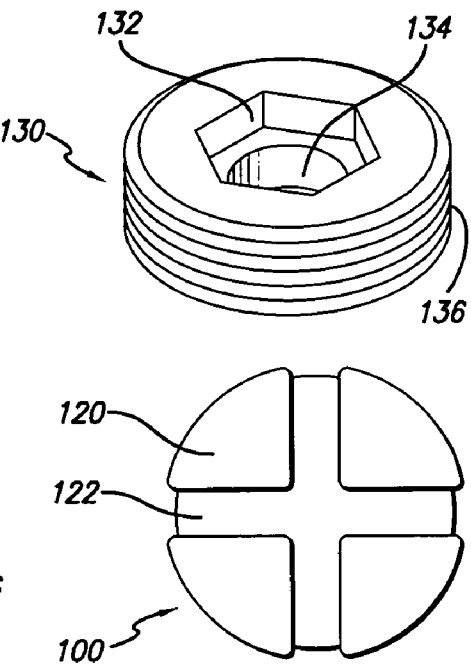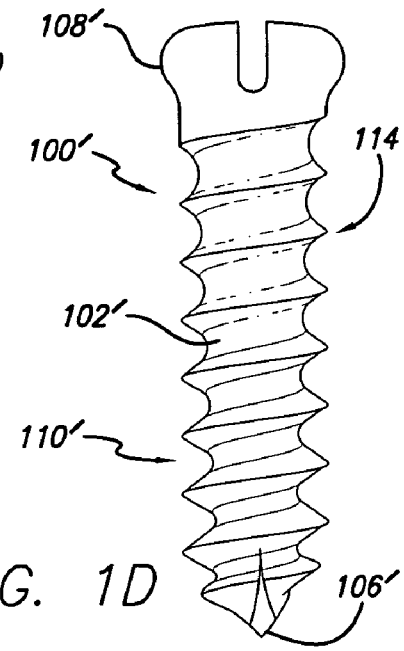

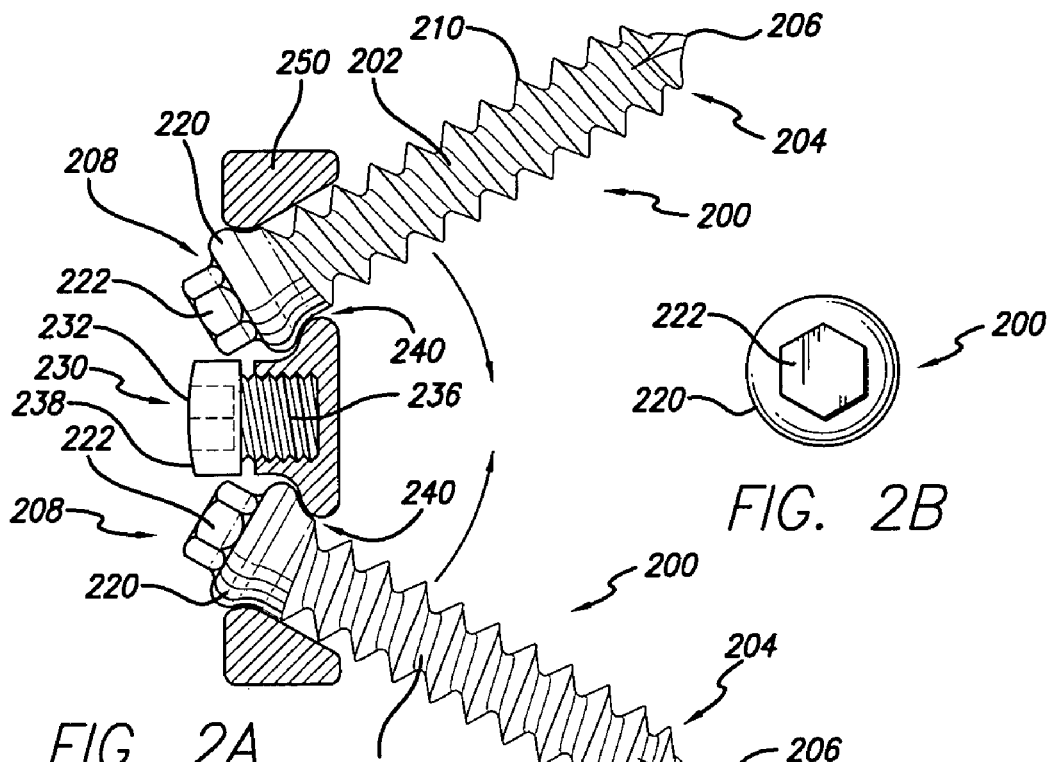
FIG. 2A
FIG. 2B
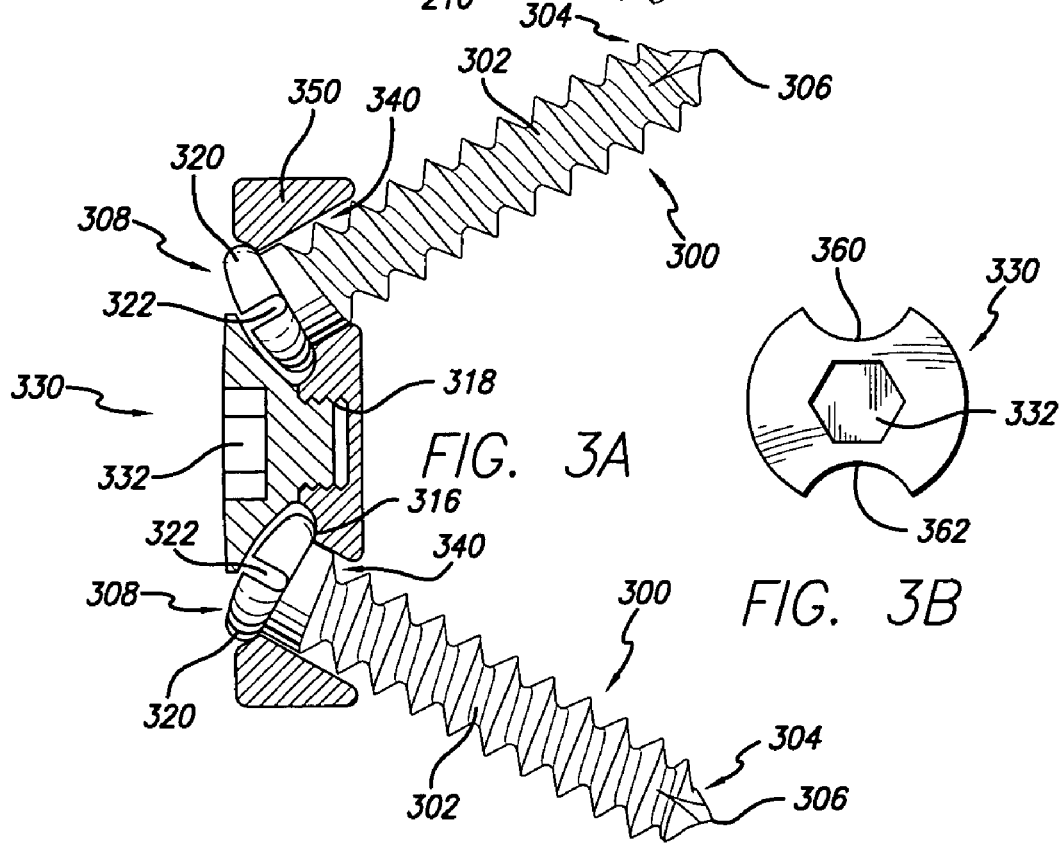
FIG. 3A
FIG. 3B

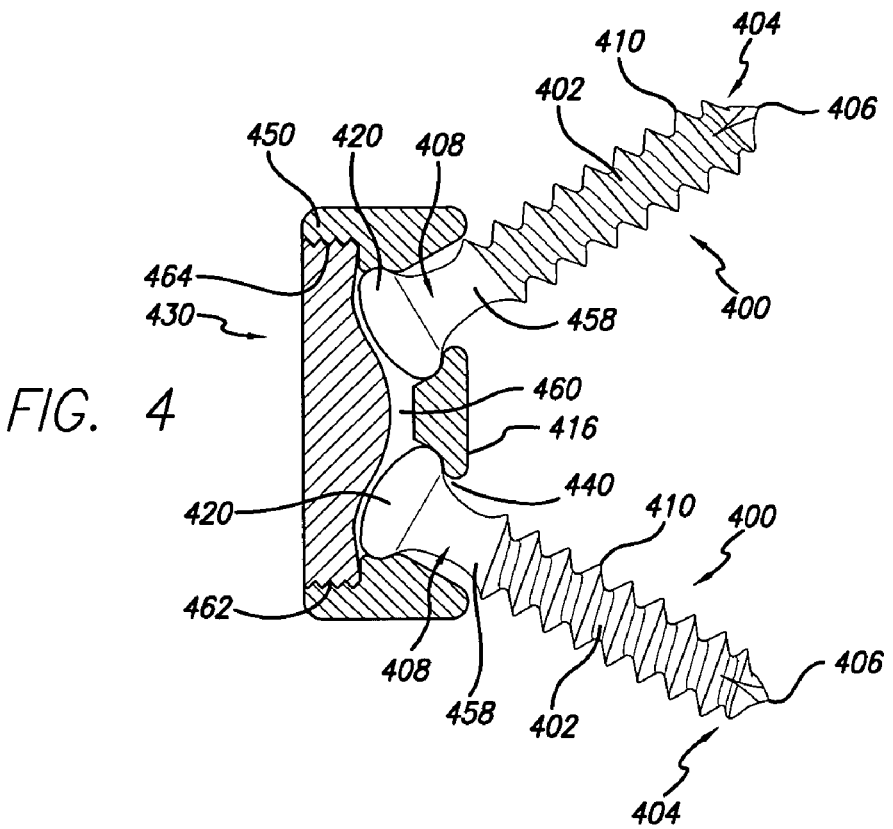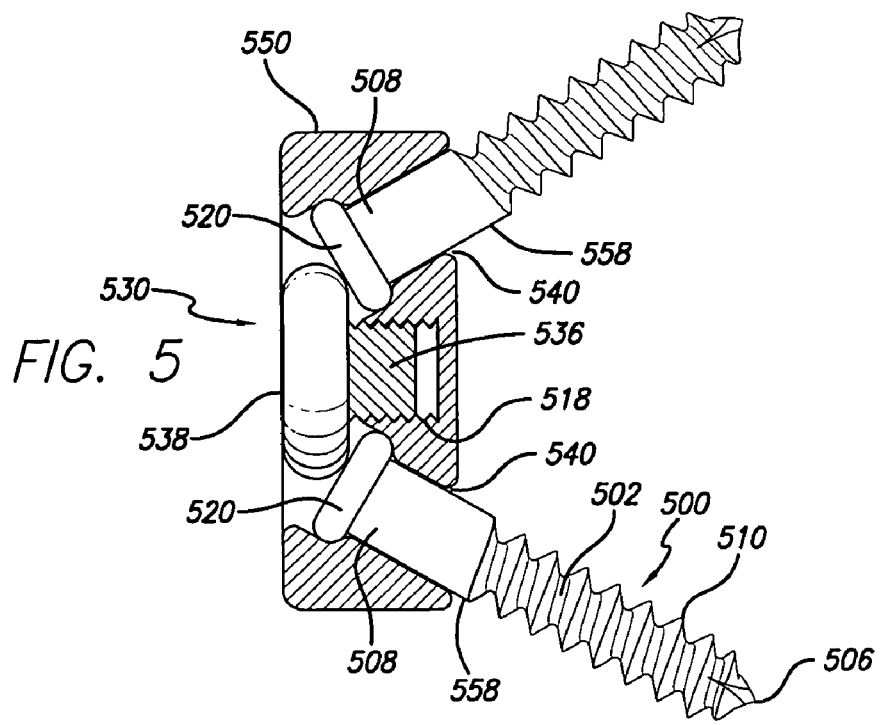

FIG. 8
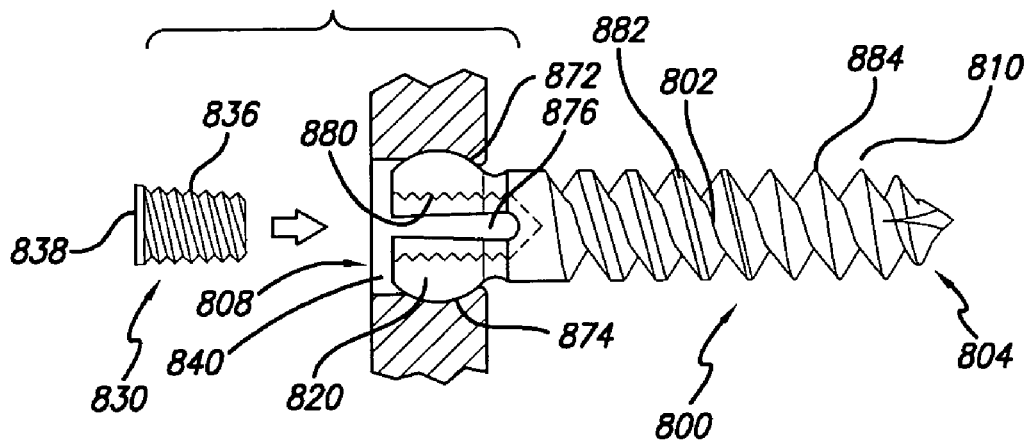
FIG. 9
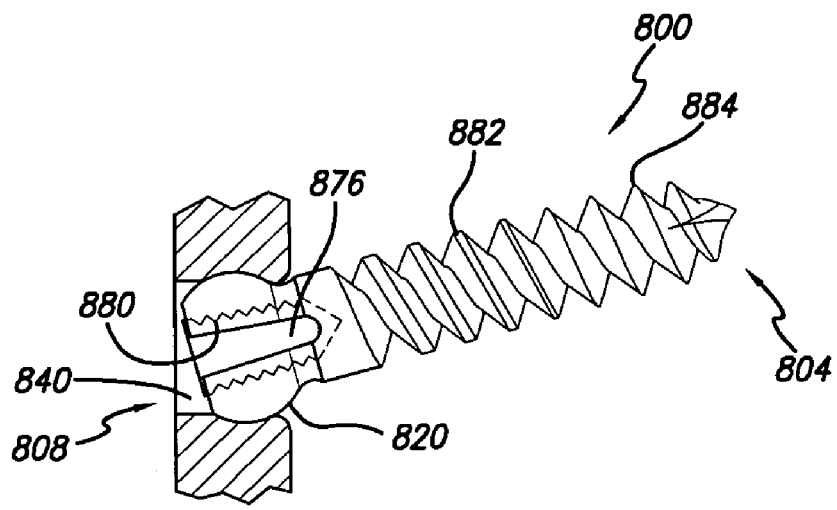
FIG. 10

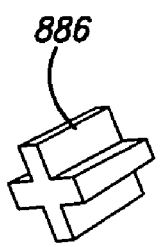
FIG. 13
FIG. 14
FIG. 12
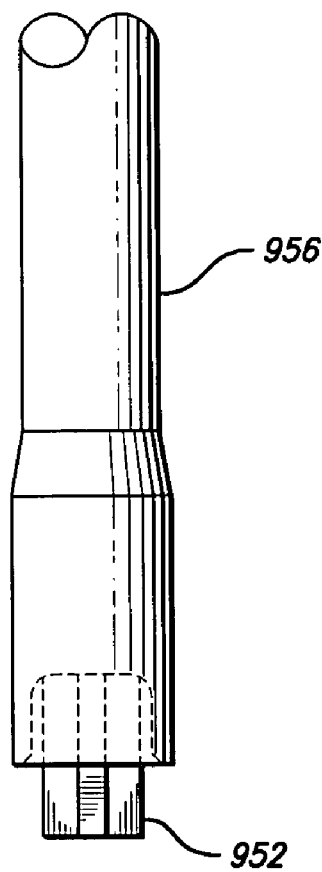
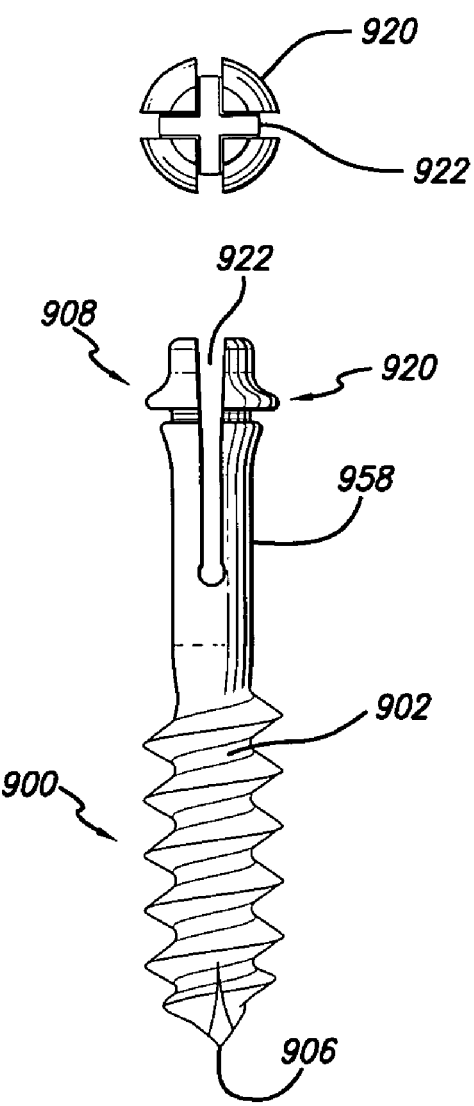
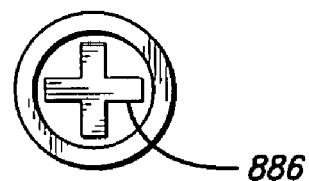
FIG. 15
FIG. 11

SCREWS OF CORTICAL BONE HAVING A TRAILING END CONFIGURED TO COOPERATIVELY ENGAGE AN IMPLANT

RELATED APPLICATION

This is a divisional of application Ser. No. 09/566,055, filed May 5, 2000, which claims the benefit of U.S. provisional application No. 60/132,671, filed May 5, 1999; all of which are incorporated herein by reference.

BACKGROUND OF THE INVENTION

1. Field of the Invention

This invention is directed generally to screws for orthopedic use in humans, and specifically to screws made of cortical bone and method of manufacture thereof.

2. Description of the Related Art

The mammalian skeleton includes dense structural bone known as cortical bone. In humans, the femur, one of the larger long bones of the body, may have a cortical thickness as great as 6-8 mm. Larger mammals, which have been used to provide bone for surgical use in humans, have bones with cortical thicknesses substantially greater than those found in humans.

Screws for orthopedic use may be used for a multitude of purposes, including to join separated bone portions, and to attach various orthopedic implants, such as skeletal plates, to bones. Such screws have commonly been made of surgical quality metals (e.g. stainless steel, surgical grade titanium, and titanium alloys), ceramics and various plastics including some that are bioresorbable.

Metal screws typically remain in the body unless explanted by a later, separate operative procedure, and can inter alia potentially irritate tissue proximate the metal screws, shed ions harmful to the body, back-out or loosen causing injury within the body. Metal screws also can interfere with optimal visualization of the affected area by various diagnostic modalities such as x-rays, CAT scans or MRIs. On the other hand, resorbable screws made of bioresorbable plastic materials which can be absorbed by the body over time have had both limited applicability and success. Resorbable plastic screws have often been limited by insufficient strength, an inability to be formed into a sharp thread-form, an unpredictable absorption rate, an inability to maintain sufficient structural integrity for an adequate period of time, the elicitation of an undesirable inflammatory response, and the potentially toxic effects of the degradation products of the material released by the bioresorption process.

There is therefore a need for a bone screw that combines the advantages of being sufficiently strong so as to be useful for skeletal fixation and for the attachment of various implants to the human skeleton, that additionally is resorbable within the body, and which does not have all the undesirable qualities encountered with screws of the past.

SUMMARY OF THE INVENTION

In accordance with the present invention, as embodied and broadly described herein, there are provided bone screws made of cortical bone for orthopedic use in humans. In a preferred embodiment, the bone screw of the present invention is made substantially of cortical bone and comprises at least a partially threaded shaft that is substantially solid, a leading end for introduction of the screw, and an opposite trailing end. The trailing end is adapted to cooperatively engage an instrument for turning the screw. The trailing end further comprises a head configured so as not to be able to pass through the same opening and passageway of an implant, for example, that the threaded shaft portion of the screw is capable of passing through for the purpose of preventing the continuing advancement of the screw. The screw head may take the form of an enlargement having either a greater diameter or a greater maximum dimension than that of the outer diameter of the threaded shaft portion of the screw. In the alternative, the proximal shaft portion at the trailing end of the screw may have a thread pitch in which the thread crests are closer together than the thread crests proximate the leading end. In a further refinement of this alternative, it is possible for the outside diameter of the thread to remain constant over the length of the screw shaft and for the thread profile to change from a cancellous thread-form for engaging cancellous bone to a machine thread-form at the trailing end to lock the screw at or within an orthopedic implant or at the cortex of a recipient bone itself.

The present invention is directed to an orthopedic bone screw made substantially of cortical bone, which is preferably but not necessarily of human origin. The screw of the present invention is substantially solid throughout its shaft portion and has a head portion at its trailing end configured to resist the further forward advancement of the screw when the screw is threaded through an appropriately sized opening, such as an opening in an orthopedic implant.

While the present invention is not so limited, the preferred bone is human obtained from the diaphyseal region of one of the large tubular bones of the skeleton, such as the femur or from a portion of a generally intramembraneously formed substantially cortical bone, such as may be found in the skull.

The present invention is further directed to locks for locking bone screws to an implant as an element separate from the screw or as part of the screw itself. The locks preferably also are made of cortical bone for locking the screws to an implant. The present invention also includes the combination of screws and locks with an orthopedic implant which also is preferably made of cortical bone.

The accompanying drawings, which are incorporated in and constitute a part of this specification, are by way of example only and not limitation, and illustrate several embodiments of the invention, which together with the description, serve to explain the principles of the invention.

BRIEF DESCRIPTION OF THE DRAWINGS

FIG. 1A is a side elevation view of a first embodiment of a bone screw, a screw lock in cross section both made of cortical bone, a partial cross section of an orthopedic implant, and a tool in fragmentary view for installing the bone screw and screw lock.

FIG. 1B is a top perspective view of the lock of FIG. 1A.

FIG. 1C is a top plan view of the screw head of the bone screw of FIG. 1A.

FIG. 1D is a side elevation view of another embodiment of the bone screw in accordance with the present invention.

FIG. 2A is a side elevation view of a second embodiment of two bone screws and a screw lock made of cortical bone in accordance with the present invention, and a partial cross section of an orthopedic implant.

FIG. 2B is a top plan view of the head of a bone screw in FIG. 2A.

FIG. 3A is a side elevation view of a third embodiment of two bone screws and a screw lock made of cortical bone, and a partial cross section of an orthopedic implant.

FIG. 3B is a top plan view of the screw lock of FIG. 3A.

FIG. 4 is a side elevation view of a fourth embodiment of two bone screws and a screw lock made of cortical bone, and a partial cross section of an orthopedic implant.

FIG. 5 is a side elevation view of a fifth embodiment of two bone screws and screw lock made of cortical bone, and a partial cross section of an orthopedic implant.

FIGS. 8–10 are side elevation views of an eighth embodiment of a bone screw, and a screw lock made of cortical bone, and a partial cross section of an orthopedic implant.

FIG. 11 is a side elevation view of a ninth embodiment of a screw made of cortical bone.

FIG. 12 is a top plan view of the trailing end of the bone screw made of cortical bone shown in FIG. 11 with a locking insert therein.

FIG. 13 is perspective view of a locking insert of cortical bone for use with the bone screw shown in FIGS. 11 and 12.

FIGS. 14 and 15 are a side elevation view and an end view, respectively, of an instrument for inserting the bone screw of FIGS. 11 and 12.

DETAILED DESCRIPTION OF THE DRAWINGS

Figure 6:
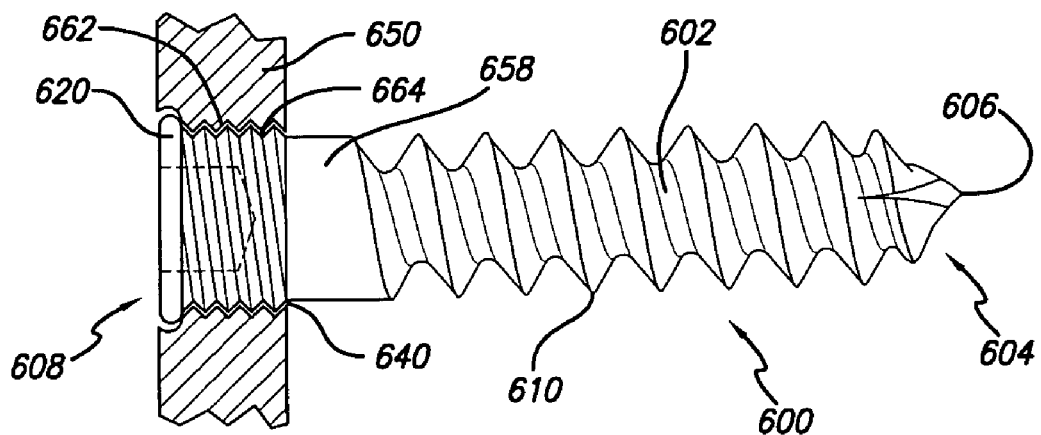
FIG. 6 is a sixth embodiment of a bone screw and a partial cross section of an orthopedic implant each made of cortical bone.

The following description is intended to be representative only and not limiting and many variations can be anticipated according to these teachings, which are included within the scope of the present invention. Reference will now be made in detail to the preferred embodiments of this invention, examples of which are illustrated in the accompanying drawings.

FIGS. 1A–12, 18, 21, and 22 show various embodiments of screws made of cortical bone in accordance with the present invention generally referred to by the reference numerals 100 to 1100, respectively. Similar reference numbers will be used throughout the drawings to refer to similar portions of similar parts.

Screws 100–1100 are shown in use with partial segments of orthopedic implants generally referred to by the reference numerals 150–850. As used in this application, orthopedic implants 150–850 can include various types of orthopedic implants such as, but not limited to, skeletal plates and interbody spinal fusion implants. Orthopedic implants 150–850 are preferably made of resorbable (bioresorbable) materials such as, but not limited to, cortical bone, plastics, and composite plastics. Suitable plastics may include those comprising lactides, galactides, glycolide, capronlactone, trimethylene carbonate, dioxanone in various polymers and/or combinations. Implants 150–850 may also comprise any other material suitable for surgical implantation into the human body including various metals, ceramics, and non-resorbable plastics and composites.

Screws 100–1100 each have a shaft that is threaded at least in part preferably having a tip at its leading end and may have a screw head at its trailing end. The screw head may or may not be protuberant, but is adapted to prevent the forward movement of the screw once the head is fully engaged to the orthopedic implants 150–850 or an appropriate opening in a bone.

Screws 100–1100 may be further secured to the orthopedic implants 150–850 by locks that are preferably made of cortical bone and may also be made of resorbable materials.

FIGS. 1A–1C show a screw 100 with a shaft 102 having a leading end 104, a tip 106, and a trailing end 108 opposite leading end 104. Shaft 102 is configured to pass through an opening 140 in an implant 150 adapted to receive a bone screw. Shaft 102 has a thread 110 adapted to engage bone. Shaft 102 has a minor diameter and an outer diameter as measured from the peaks of threads 110 to the minor diameter. The turns of thread 110 are spaced apart by valleys preferably having rounded bottoms. As a result, thread 110 has a wide base. The preferred embodiments of the present invention have generally enlarged root diameters to increase their strength overall and to withstand the torques generated on insertion which may be further mitigated by the prior use of a tap. Further stress risers are avoided by avoiding sharp corners and unradiused edges. Further, it may be desirable to have the root diameter be generally increased nearer to the head end of the screws. Thread 110 preferably has a self-tapping first turn near tip 106.

As shown in FIG. 1D, in another embodiment screw 100' has a thread near tip 106' in the same configuration of thread 110 and has a thread portion 114 with a wider base such that the valleys between thread 114 are more rounded than the valleys between the portion of thread 110'. This results in a screw having a shaft 102' with wider root diameter proximate trailing end 108' for increased strength of screw 100'. Trailing end 108 preferably has a screw head 120 with an enlarged portion having a diameter greater than the outer diameter of the threaded portion of shaft 102 and greater than opening 140 in implant 150 so as to prevent passage therethrough.

As shown in FIGS. 1A and C, screw head 120 preferably has a cruciate recess 122 for receiving distal end 152 of screw driver 156. Bone screw 100 is prevented from backing out by screw lock 130 that threads into threaded portion 118 of opening 140 in implant 150. Screw lock 130 has a tool receiving recess 132 and opening 134 for engaging lock engagement end 154 of screw driver 156 for installing screw lock 130. Distal end 152 of screw driver 156 is preferably configured to pass through opening 134 when engagement end 154 cooperatively engages recess 132.

As shown in FIG. 1A, in use distal end 152 is moved into opening 140 and screw driver 156 is utilized to insert bone screw 100 by cooperatively engaging a cruciate recess 122 in bone screw head 120. Once screw 100 is inserted into opening 140, the enlarged portion of the head 120 is at least partially blocked from passing through implant 150 by a retaining flange 116. In a preferred embodiment, lock 130 is machined out of cortical bone and may best be harvested from portions of the calvarium as it is less curved than a long bone. Alternatively, lock 130 could also be machined out of a long bone. As with other screw locks shown herein, by way of example only and not limitation, the locks can alternatively be formed of a bioresorbable plastic. Screw lock 130 is preferably made of one cortical thickness, e.g., longitudinally along a long bone, rather than by cutting transversely across the bone.

Lock 130 is preferably circumferentially threaded with threads 136 as shown in FIG. 1B. When screw driver 156 is advanced to insert lock 130 into implant 150, threads 136 of lock 130 can be threaded into receiving threads 118 of implant 150. In this example, it can be appreciated that opening 140 need not be threaded along its entire depth. Lock 130 can be rigidly tightened against the unthreaded portion of opening 140, which acts as a stop, preventing any further movement of lock 130 into opening 140. By binding lock 130 to trailing wall 112 of implant 150, and making the lower surface of lock 130 concave, allowance is made for motion of screws 100 relative to implant 150. This allows the surgeon some freedom of choice in positioning screws 100 and in selecting the direction of the force vector to be generated relative to implant 150.

Alternatively, by any number of structural configurations, such as for example an interference fit between screw head 120 and implant opening 140, or by way of more deeply threading opening 140, or by flattening the top of the screws and making the circumferential perimeter flush to lock 130, or by allowing lock 130 to contact screw head 120, later motion of screw 100 can be prevented. Stated differently, while the present example shows how to allow for variability in the screw's placement and provides for later movement of the screw as might occur with settling, in the alternative, the path of screw 100 through implant 150 can be rather narrowly defined, and any angular motion of screw 100 relative to implant 150 can be prevented.

As shown in FIGS. 2A and 2B, bone screw 200 has a threaded shaft 202, a leading end 204, a tip 206, and an opposite trailing end 208. Shaft 202 has a thread 210 adapted to engage bone. Trailing end 208 has a screw head 220 having a slightly enlarged head portion. Head portion 220 has a dimension greater than the outer diameter of the thread portion 210 of shaft 202 and greater than opening 240 in the implant 250 so as to prevent passage therethrough. Screw head 220 has a hex-shaped perimeter 222 adapted to complimentary engage a hex socket driver for installing the screw. A screw lock 230 having a threaded shaft 236 and an enlarged head 238 is used to lock screws 200 to implant 250 and to prevent them from backing out. Screws 200 are preferably non-parallel to the longitudinal axis of implant 250, more preferably at an angle of between 25° and 75° relative to the implant longitudinal axis. Lock 230 includes a hexagonal tool receiving area 232 for rotatably inserting lock 230 in implant 250. Screws 200 are adapted to angle toward each other in the direction of the arrows in FIG. 2A.

As shown in FIGS. 3A and 3B, each one of bone screws 300 has a threaded shaft 302 having a leading end 304, a tip 306, and an opposite trailing end 308. Shaft 302 has a thread 310 for engaging bone. Trailing end 308 has a screw head 320 having an enlarged portion with a diameter greater than the outer diameter of the threaded portion of shaft 302 and greater than opening 340 in implant 350 so as to prevent passage therethrough. Screw head 320 has a cross slotted cruciate recess 322 similar to that shown in FIG. 1C for receiving end 152 of screw driver 156. Bone screw 300 is prevented from backing out by screw lock 330 that threads into threaded opening 318 of implant 350. The bone screw lock 330 has a tool receiving recess 332 for engaging end 352 of a screw driver for installing the screw lock 330. Screw lock 330 may also have cutaway portions 360 and 362 to permit the insertion of bone screws 300 into openings 340 while screw lock 330 is attached to implant 350 in an unlocked position. Screw lock 330 can be rotated to a locked position to cover at least a portion of screw heads 320 and lock bone screws 300 to implant 350.

FIG. 3A shows lock 330 in use, where it can be appreciated that head portion 320 of screw 300 is prevented from passing through implant 350 by a retaining flange 316 at the base of opening 340. It can also be appreciated that when lock 330 is fully tightened, a lower portion of the screw head can be tightened against implant 350 itself so as to, as previously described, allow for some convergent motion of the bone screws. FIG. 3B shows lock 330 having a hex well 332 therein, and opposed concave portions 360 and 362. It should be understood that various driver engaging structures are useful for the intended purpose are contemplated and within the scope of the present invention.

In a preferred embodiment, when lock 330 is one-quarter turn short of being fully tightened, openings 340 are open and unobstructed at lock 330 to permit bone screws 300 to be inserted therein. After screws 300 have been installed, lock 330 can be further tightened by turning it 90 degrees until the shaft of the lock 330 reaches the lower most internal threads 318, thereby allowing the locking screw to be solidly tightened to implant 350.

While screws 300 have freedom to move closer together, screws 300 cannot back out of implant 350 with lock 330 in place. As previously discussed, while this is considered preferable, implant 350 can be so constructed to prevent any angular freedom of screw 300 relative to implant 350. Further, implant 350 and lock 330 can be configured to cooperate to prevent any backward motion of screw head 320.

As shown in FIG. 4, screw 400 has a threaded shaft 402 having a leading end 404, a tip 406, and an opposite trailing end 408. As with all of the embodiments described herein, tip 406 may have various configurations and may or may not have cutting flutes. Such flutes may be useful when such screws are for insertion into cancellous bone. However, when the bone is dense, the use of a thread forming tap as could be made of an instrument quality metal would be preferable. The tap would cut the path for the screw to follow rather than have the screw be subjected to the forces that would be required to form thereafter.

Shaft 402 has a thread 410 for engaging bone. Trailing end 408 has a screw head 420 having an enlarged portion having a diameter greater than the outer diameter of the threaded portion of shaft 402 and greater than opening 440 in implant 450 so as to prevent passage therethrough. Bone screw 400 is prevented from backing out by screw lock 430. Lock 430 is in the form of a disc with a threaded side wall 462 capable of threadably engaging threads 464 within common opening 460. When screws 400 are locked to implant 450, screws 400 can be allowed some angular motion relative to implant 450. The screw lock 430 has a tool receiving recess for engaging the end of a screw driver for installing the screw lock 430. Screw lock 430 and implant 450 are preferably made of cortical bone.

Distal to heads 420 of screws 400 is a smooth shaft portion 458 of a lesser cross sectional dimension than opening 440 which, in combination with the available space within common opening 460 between screw head 420 and lock 430, allows for bone screw 400 to operate as a lag screw, but, nevertheless, be capable of some variability in its positioning and to still further be capable of some ability to move closer to implant 450.

FIG. 5 shows an alternative implant screw and lock arrangement for use with implant 550, or as with the lock and screw configuration of FIG. 4 with any of the other embodiments of the present invention as may be appropriate. To that end, it should be appreciated that the implants shown herein are by way of example only and without limitation to the various combinations and permutations of the various screw, lock, and implant configurations shown, as well as the substantial equivalent thereof which are within the scope of the present invention.

As shown in FIG. 5, screw 500 has a threaded shaft 502 having a leading end 504, a tip 506, and an opposite trailing end 508. Shaft 502 has a thread 510 for engaging bone. Trailing end 508 has a screw head 520 having an enlarged portion having a diameter greater than the outer diameter of the threaded portion of shaft 502 and greater than opening 540 in implant 550 so as to prevent passage therethrough. Screw head 520 is preferably adapted to cooperatively engage the end of screw driver. Bone screw 500 is prevented from backing out by screw lock 530 that has a shaft 536 that threads into internal threads 518 implant 550. As with other embodiments herein described, the screw lock 530 may have a tool receiving recess for engaging an end of a screw driver for installing screw lock 530. Screw 500 and lock 530 are preferably made of cortical bone as preferably is implant 500. The combination results in screw 500 having a precise and defined orientation that is further secured by lock 530 so that no angular deviation of the screw in the construct is allowed.

Lock 530 differs from lock 430 in that extending from head portion 520 is a threaded shaft 536 for threading into internal threads 518 between opposed openings 540 within common opening 560 of implant 550. Unlike the mechanism illustrated in FIG. 4 where cap 430 tightens against the internal implant wall rather than only pressing against the screw heads themselves, thereby permitting some motion, head 538 of lock 530 tightens against heads 520 of screws 500 which also differ from screws 400 in that the smooth proximal shaft portions 558 are adapted to form an interference fit with the passageway through implant 550 and to thereby in combination allow for the screws to have a precise trajectory and to further be rigidly locked to the implant. It should be appreciated then that FIGS. 4 and 5 each teach a structure by which an implant of the present invention can be constructed so as to either cause the screws passing therethrough to have a fixed trajectory or in the alternative, be capable of variable angle placement. Further taught is structure for permitting the present invention implants to either allow for, or to prevent post-deployment angular motion of the bone screws relative to the implant after the screws have been locked within the implant; or still further to allow for but one degree of freedom of the locked screws and that being only to allow for the settling, or the coming closer together of the adjacent vertebrae. Various ways for achieving each of these are shown herein and may be combined in various ways with various embodiments of the implants shown or their substantial equivalents without departing from the scope of the present invention.

As shown in FIG. 6, screw 600 has a threaded shaft 602 having a leading end 604, a tip 606, and an opposite trailing end 608. Shaft 602 has a first thread 610 for engaging bone. Trailing end 608 has an enlarged portion 620 having a diameter greater than the outer diameter of the threaded portion of shaft 602 and greater than opening 640 in the implant 650 so as to prevent passage therethrough. Opening 640 is preferably threaded. Proximate enlarged portion 620 is a second thread 612 having a different thread pitch than thread 610. For example, thread 610 could have a thread pitch similar to a wood screw and thread 612 could have a thread pitch similar to a metal screw. Screws 600 are self locking as a result of the different thread pitches of screw 600 in combination with thread opening 640. That is the combination of screw 600 with implant 650 adapted to receive that screw, obviates the need for a third element such as a lock, and functions to achieve locking by the interaction of the two elements.

Figure 7A:
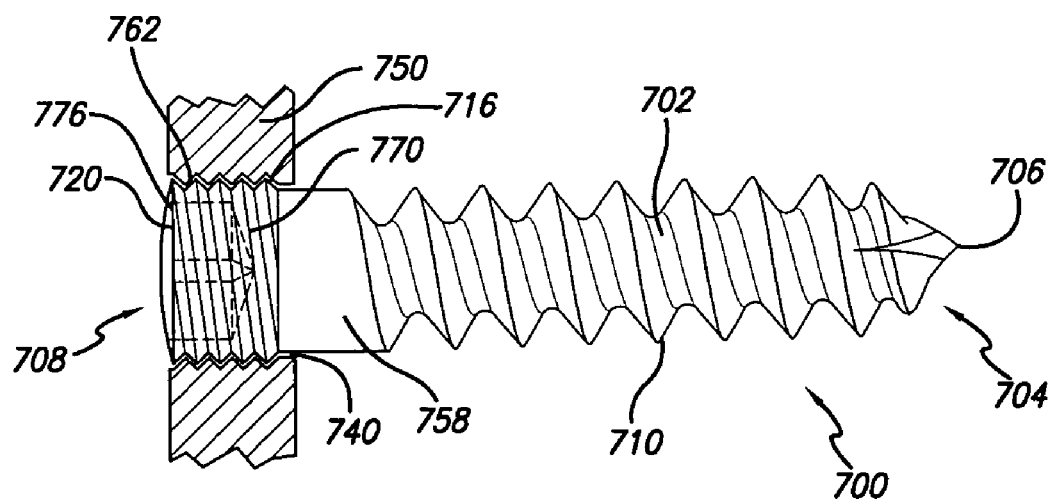
FIG. 7A is a side elevation view of a seventh embodiment of a bone screw and a partial cross section of an orthopedic implant lock made of cortical bone.
Figure 7B:
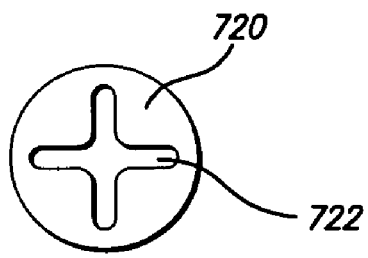
FIG. 7B is a top plan view of the trailing end of the screw in FIG. 7A.

As shown in FIGS. 7A and 7B, screw 700 has a threaded shaft 702 having a leading end 704, a tip 706, and an opposite trailing end 708. Shaft 702 has a first thread form 710 for engaging bone. Trailing end 708 has an enlarged portion 720 having a diameter greater than the outer diameter of the threaded portion of shaft 702 and greater than opening 740 in implant 750 so as to prevent passage therethrough. Opening 740 is preferably threaded at least in part. Enlarged portion 720 has a second thread 712 having a different thread pitch than thread 710. For example, thread 710 could have a thread pitch similar to a wood screw and thread 712 could have a thread pitch similar to a metal screw.

Unlike screw 600, screw 700 does not have an additional enlarged head portion such as portion 620 of screw 600, but rather relies on flange portion 716 of opening 740 to stop the further progression of the screw head 720 through the implant and to allow for head 720 to be securely tightened to the trailing end of implant 750. Screw head 720 can preferably have a cruciate recess 722 for receiving the end of screw driver.

FIGS. 8–10 show an alternative embodiment of a locking screw mechanism which can be adapted for use with various of the other shown and/or described implant embodiments and other interbody spinal fusion implants of the present invention. Portion 808 of implant 850 has an opening 840 for accepting a bone screw 800. Bone screw 800 has a head portion 820 having at least in part about its perimeter a convex surface 872 having a maximum diameter. Bone screw receiving opening 840 has a circumferential concavity 874 for receiving convexity 872 of bone screw head 820. Bone screw head 820 has threads 880 and a plurality of slots 876, preferably two to four. Slots 876 allow locking screw 830 to cooperatively engage and be driven with a driver and allow for head 820 to sufficiently compress to be fully received within opening 840 of implant 850.

As can be appreciated from FIGS. 8–10, screw 800 can be placed at an angle to implant 850. Once bone screw 800 has been fully engaged into a bone such as an adjacent vertebral body, for example, the screw can be further rotated, allowing the vertebral body to be lagged to implant 850, increasing the compressive load. Once screw 800 has been properly placed and tightened to the extent desired by the surgeon, a locking screw 830 having a head 838 and a threaded shaft 836 may be threaded into the threaded interior of bone screw head 820 via interior threads 880.

The implant screw locking system of FIGS. 8–10 can be manufactured such that while the locking screw 830 may be lockably tightened to bone screw 800, and thus the backward migration of 800 from implant 850 prevented, the system can be designed so as to either allow for angular motion after locking screw 830 is locked to bone screw 800 or to prevent it. The function of bone screw head 820 in its ability to rotate and angulate within implant 850 is not dissimilar to the above described variation of the self-locking screw.

Also shown in FIGS. 8–10 are the degrees of sharpness of the arcuate portion of thread 810, or decreasing thread pitch along shaft 802 towards trailing end 808. Beginning from the leading end 804 and extending towards trailing end 808, thread 810 progressively becomes thicker until at, for example, location 882 thread 810 is thicker at its outer diameter than at location 884. The thickening increases more towards trailing end 808. By having a sharp thread pitch 884 near leading end 804 and a progressively less sharp thread pitch extending towards the trailing end, screw 800 embeds itself more securely. Thread portion 882 expands the V-cut left by the sharper thread portion 884, thereby adding force vectors substantially parallel to the screw longitudinal axis and further tightening the fit of screw 800 within a bone.

FIGS. 11–13 show a screw 900 having a threaded shaft 902 with leading end 904, tip 906, and an opposite trailing end 908. Shaft 902 has a thread 910 for engaging bone. Trailing end 908 has a screw head 920 having an enlarged portion with a diameter greater than the root diameter of shaft 902. Screw head 920 preferably has a cruciate recess 922 for receiving an insert for spreading apart cruciate recess 922 to expand enlarged portion 920 to a dimension larger than the outer diameter of thread 910. Recess 922 is adapted to cooperatively engage projection 886 of screw driver end 952. Engaging projection 886 extends along the longitudinal axis of screw driver 956. In use, engaging projection 886 will slidably engage with recesses 922 and screw head 920. The extended length of engaging projection 886 allows the surgeon to more forcefully and securely apply a rotative force upon screw 900. Although a cruciate or "plus sign" configuration is illustrated for engaging projection 886, a wide range of alternatives are available and contemplated by the scope of the present invention.

Tool 956 may be manual or powered. Tool 956 preferably has a push-down inner shaft connected to engaging projection 886 so that in use, the surgeon will push down on tool 956 and rotate to insert screw 900. Alternatively, if tool 956 is electrically powered, an inner shaft connected to engaging projection 886 may be made to rotate upon the surgeon pushing down on the tool after proper positioning. Although a tool with a push down inner shaft is preferred, it is not required. For example, engaging portion 886 may be fixedly attached within tool 956.

Figure 16:
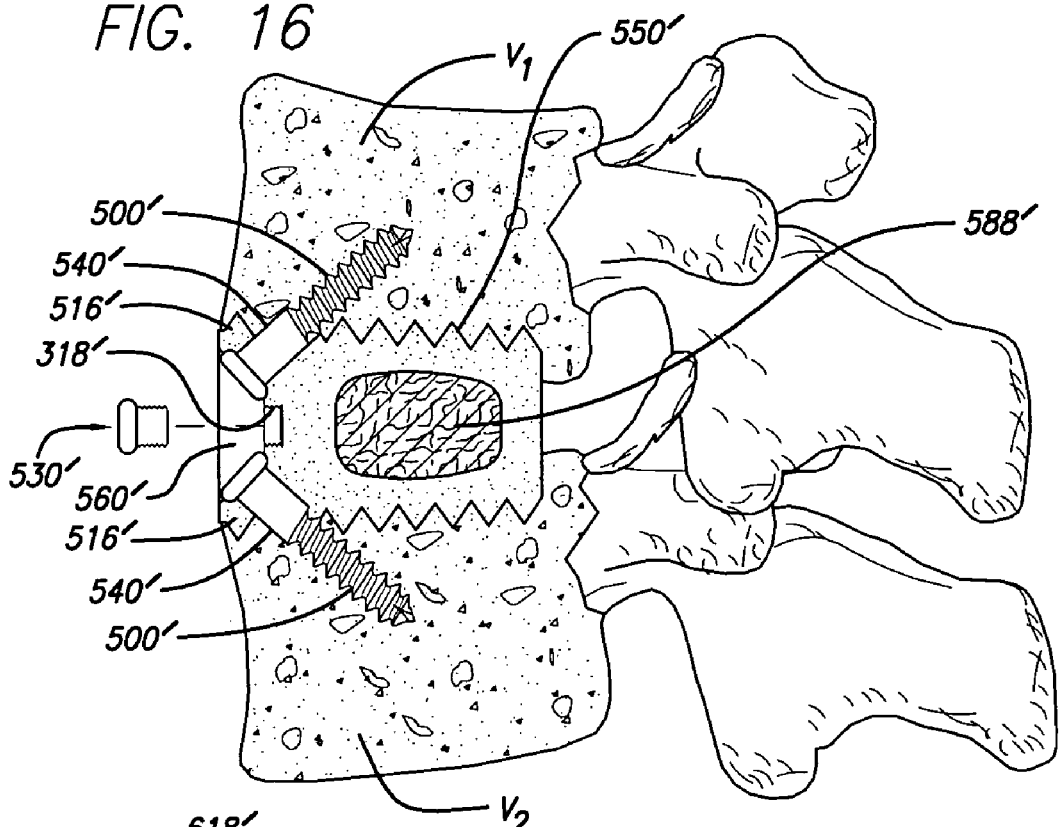
FIG. 16 is a side elevation view in partial cross section of a segment of the human spine with a spinal fusion implant made of in partial cross section bone inserted between two adjacent vertebrae, bone screws of FIG. 5, and a screw lock being installed.

FIG. 16 shows an embodiment of the present invention with implant 550' properly implanted across the disc space between adjacent vertebral bodies $V_1$ and $V_2$. Openings 588' of implant 550' allow for vascular access through trailing end 512' of implant 550' and for bone growth therethrough. Trailing end 512' has common opening 560' and situated essentially therein, is threaded opening 318' for receiving an implant driver. The implant driver has a distal end for a complimentary fit within common opening 560' and therethrough a rotatable threaded member for threading into opening 318'. Internal threads 318' of implant 550' are configured to receive lock 530' in a way similar to that illustrated in FIG. 5. Opening 560' also is adapted to receive a screw device to link the implant to other implants, to a staple, or to receive a locking screw to lock bone engaging screws to the implant as disclosed Michelson U.S. patent application Ser. No. 08/926,334 incorporated herein by reference. Common opening 560' also may have therein opposed and divergently angled openings 540' adapted to receive opposed vertebral bone engaging screws 500'. Bone screw receiving openings 540' preferably may have circumferentially around them retaining seats 516' adapted to receive and to block the passage of the heads of screws 500' to be inserted therethrough. Retaining seats 516' may also be flanged.

Figure 17:
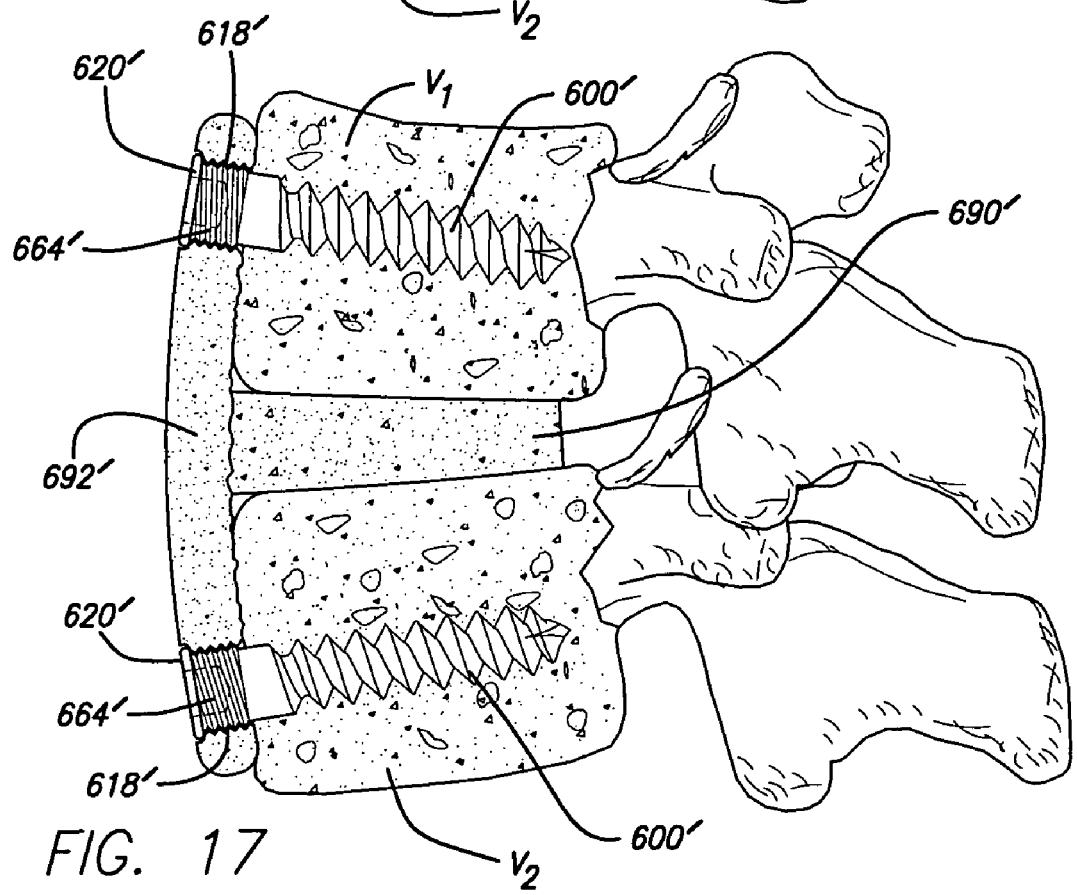
FIG. 17 is a side elevation view in partial cross section of a segment of the human spine with an orthopedic plate in cross section made of bone placed across a spinal disc in contact with the adjacent vertebral bodies and screws installed through the orthopedic plate and into the adjacent vertebral bodies.

FIG. 17 shows screws 600' of the present invention used with a plate 692' and an implant 690' inserted into the disc space between adjacent vertebral bodies $V_1$, $V_2$. Preferably, both plate 629' and implant 690' are formed of bone. Screws 600' may have a dual-threaded shaft. That is, the leading end may be threaded for engaging cancellous bone while the trailing end may be separately threaded for engagement with bone plate 692'. Preferably, an unthreaded shaft portion 658' is between the threaded shaft portions. In this embodiment, flange 618' in plate 692' will act as a stop to the enlarged portion of screw head 620'.

Figure 18:
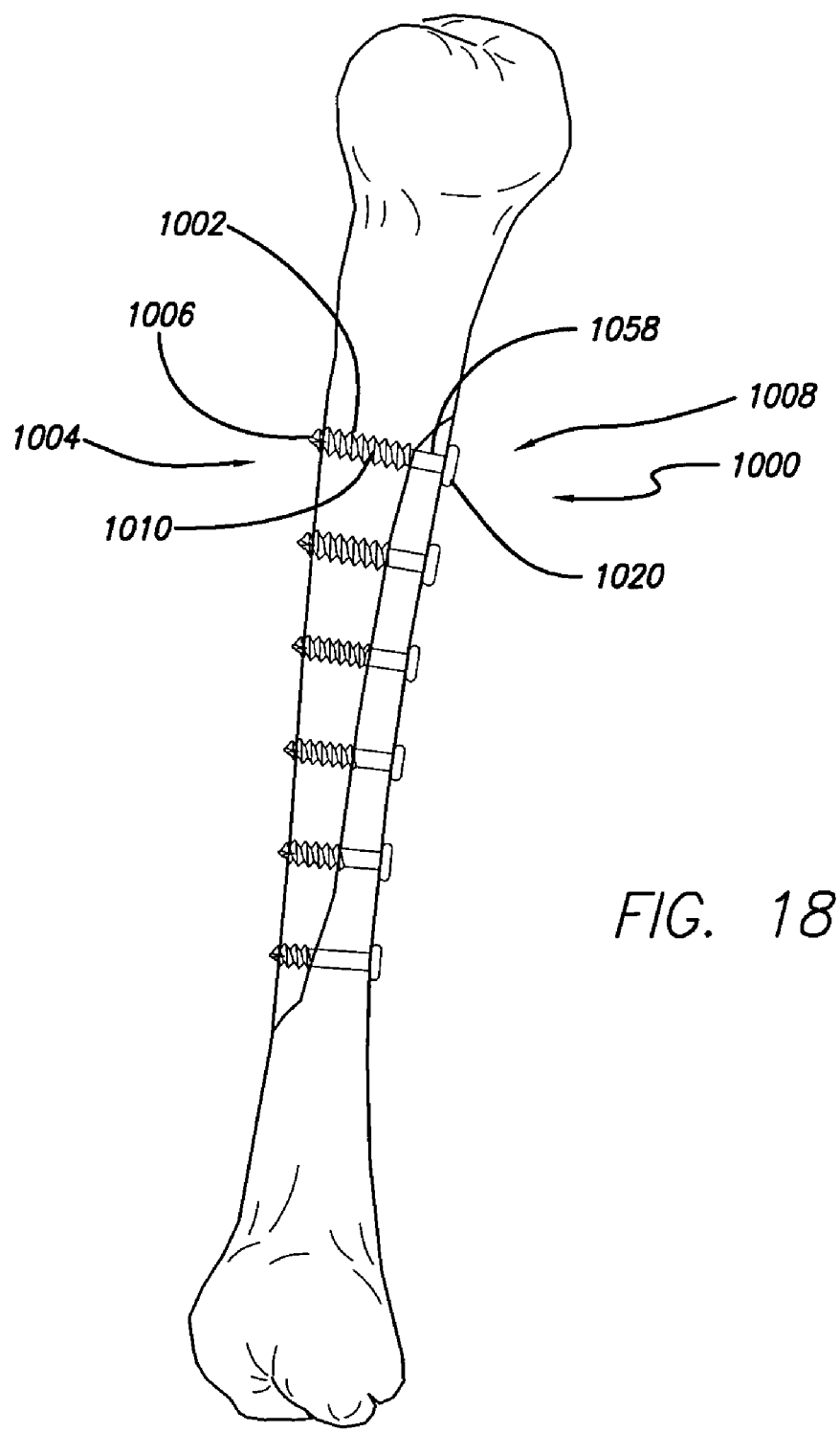
FIG. 18 is a side elevation view of a fractured long bone with lag screws made of bone in accordance with the present invention installed along the fracture to rejoin the long bone.

FIG. 18 shows a fractured bone screwed together with lag screws 1000 having different ratios of threaded to non-threaded shaft lengths. The surgeon may select screws based on the depth of the bone and the location of the fracture. By selecting screws with a non-threaded shaft length 1058 near trailing end 1008 to match the first, proximate fractured bone portion, the surgeon can insert substantially all the threaded shaft length 1002 at the leading screw end 1004 into the second, more distal fractured bone portion. In a manner similar to embodiments described before, an enlarged portion of screw head 1020 cooperates with the outer surface of the bone to assist in locking the first, proximate bone portion with the second, distal bone portion. Selecting screws of varying ratio between threaded and non-threaded length to approximate the facture line will result in a more secure fit and ultimately enhance the bone healing process. The placement of smooth portions of screws 1000 in one fractured portion and threaded portions in the other fractured portion permits the pulling together or "lagging" of the two fractured bone portions.

Figures 19, 20, 21, 22:
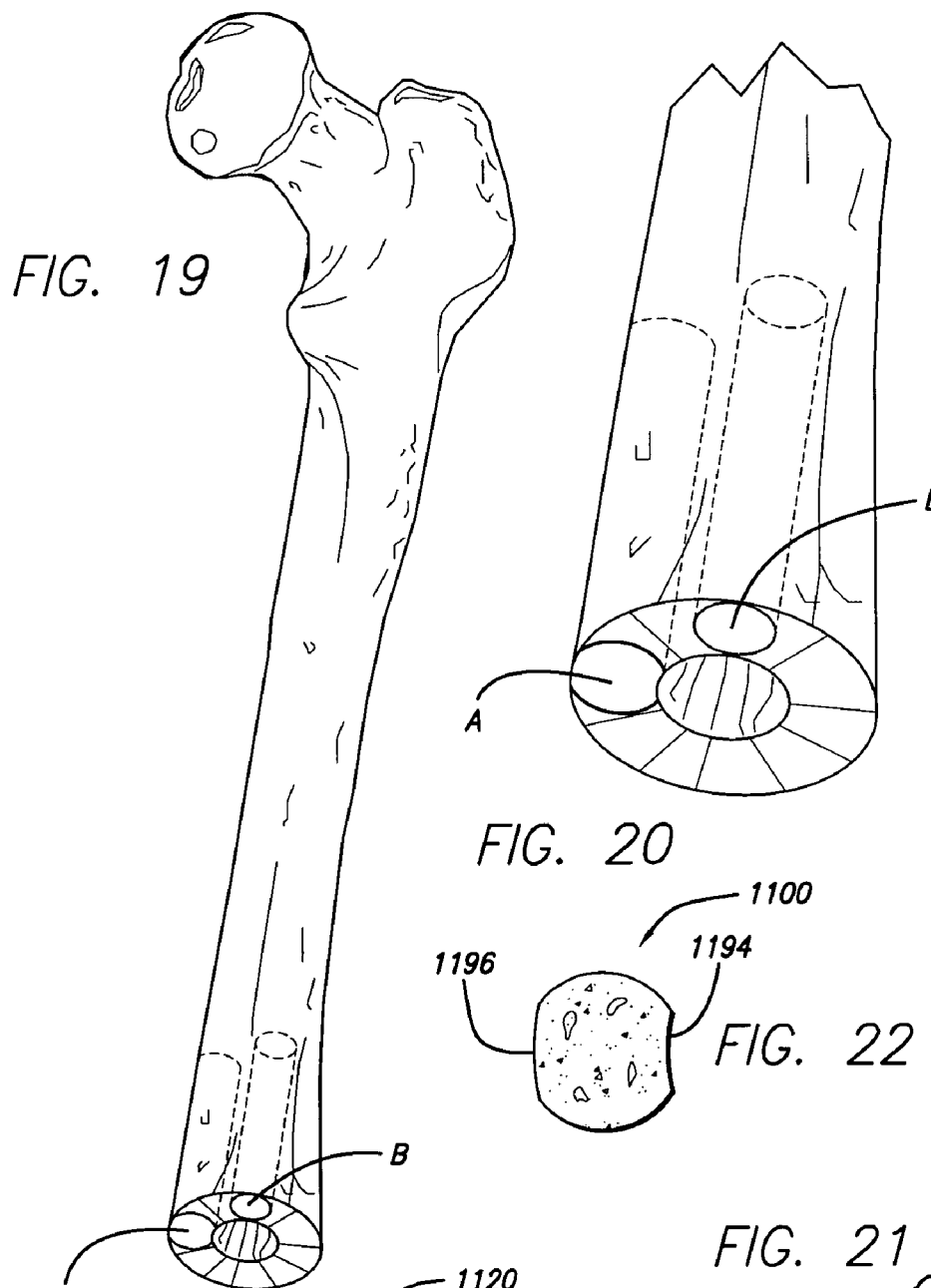
FIG. 19 is a side elevation view of a long bone with segments illustrated in hidden line of cortical bone being removed from the diaphysis by making a longitudinal cut, the segments being used to form bone screws made of cortical bone in accordance with the present invention.
FIG. 20 is an enlarged fragmentary end view of FIG. 19.
FIG. 21 is a side elevation view of a tenth embodiment of a bone screw made of cortical bone removed from the diaphysis of a long bone in accordance with the present invention.
FIG. 22 is an end view of a segment of cortical bone removed from the diaphysis of a long bone by making a longitudinal cut as illustrated in FIG. 20.

FIGS. 21 and 22 show a cortical bone screw 1100 having a shaft 1102 with thread 1110 configured with both a concavedly arcuate portion 1194 and a convexedly arcuate portion 1196 along a transverse cross section to the longitudinal axis of the screw. Preferably, concave and convex portions 1194, 1196, respectively, are opposite each other as shown in FIG. 22. The concave and convex portions may be formed by cutting a strip A from a long bone as shown in FIG. 20 with a trephine having a diameter greater than the cortical thickness of the bone. The concave portion can correspond to the area of bone facing the medullary canal. Screw head 1120 may also have concave and convex portions aligned with those of shaft 1102. The radii of the concave portions may vary along the length of the longitudinal axis. The radii of each concavedly arcuate portion 1194 and convexedly arcuate portion 1196 may also vary in relation to each other along a plane transverse to the longitudinal screw axis. Although screw 1100 may be made from many different materials, it is preferred that screw 1100 is formed substantially of cortical bone of a single cortical thickness. Screw 1100 may also include a recess 122 for engagement with a tool such as one hereinbefore described.

For the embodiments of bone screws described herein, by way of example, the bone screws of the present invention for use in the lumbar spine would have an outer diameter in the range of approximately 4 to 8.5 mm, with approximately 5 to 7.5 mm being preferred; and an overall length in the range of approximately 20 to 40 mm, with approximately 25 to 30 mm being preferred.

For use in the cervical spine, an outer diameter in the range of approximately 3 to 6 mm, with approximately 4 to 5 mm being preferred; and a length in the range of approximately 10 to 20 mm, with approximately 12 to 16 mm being preferred.

By way of example, a bone screw of the present invention for use in the lumbar spine could have a root diameter of approximately 5 mm and an outer diameter of approximately 7.5 mm; a thread pitch of approximately 3 mm distally and at the trailing end by use of a multipoint lead, a triple wound thread having a pitch of approximately 1 mm. Such a screw could be threaded through an opening in a material having a thickness less than the 3 mm of the distal screw pitch and an opening greater than the root diameter, but less than the outer diameter, until such screw was threaded into the point where the three point lead at the trailing end of the screw engaged the threaded opening in the material. At which point, the screw would be lockably engaged into the material as the wall thickness of the material into which the screw was being threaded would no longer fit between the individual threads of the machine threaded portion of the screw.

Alternatively, the pitch of the screws could progressively decrease towards the trailing end, or the threads thicken to the same effect. In a further embodiment of the present invention, the head of the screw could be slightly flared, with or without expansion/compression slots therethrough, such that when the head is tightened into the implant, the head is compressed and wedged into a high interference fit to the implant stopping the further forward motion of the screw and locking it therein.

These screws may be cut from a single thickness of cortex as distinct from cutting transversely across a long bone so as to include a significant hollow within the screw as a result of the medullary canal of that long bone.

Figure 23:
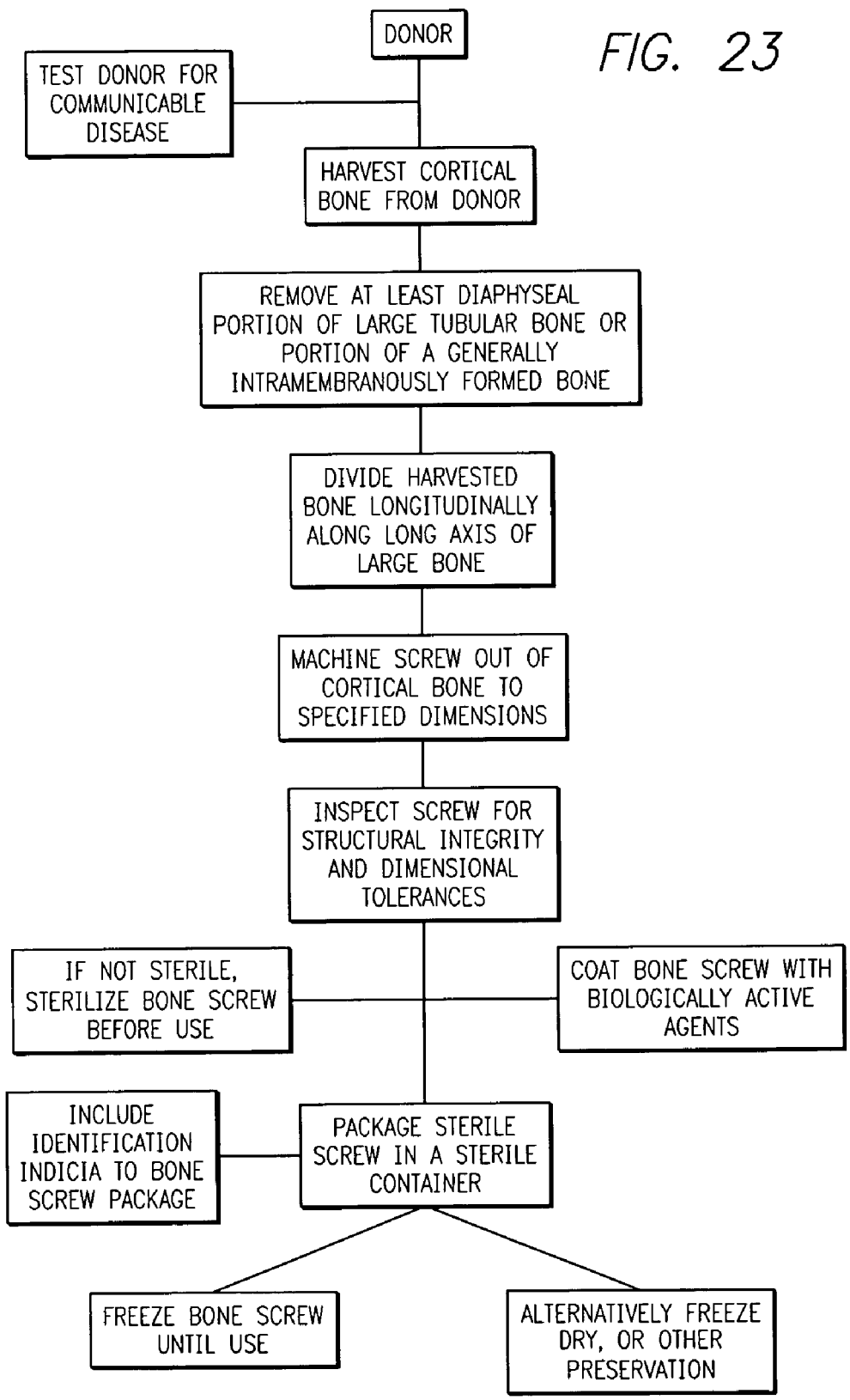
FIG. 23 is a block diagram of the steps of manufacturing and packaging the bone screws of the present invention.

Referring to FIGS. 19, 20 and 23, in a preferred method of manufacturing the bone screws of the present invention, bone is harvested sterilely from a donor such as a human cadaver for example, and further manufactured using sterilized machinery.

Referring to FIGS. 19 and 23, in a first step at least a diaphyseal portion of a large tubular bone or a portion of a generally intramembraneously formed bone such as the calvarium is removed from a human cadaver preferably, but not necessarily, in a sterile manner.

As illustrated in FIG. 20, in a second step the harvested bone is further divided longitudinally along the long axis of the large bone and preferably, but not necessarily, into strips having a width generally as great or slightly greater than the thickness of the cortical bone. For example, strips A and B may have the configuration shown in FIGS. 19 and 20. While the bone can be cut using any appropriate type of cutting device such as a saw, laser, water jet, etc., a hollow tubular cutter such as a trephine having an inside diameter sized to match the outer diameter of the screw to be made or greater, the thickness of the donor cortex, or slightly greater than the thickness of the donor cortex is particularly beneficial as it provides for a generally more or less circular cross section that facilitates the further machining of the threads therefrom. It should be understood that the bone diaphysis can be cut to length prior to or after the forming of the longitudinal strips.

In a third step, a machine appropriate for machining a screw such as a lathe, a Swiss milling machine, a CNC, a thread whirling machine, or similar device is used to machine the screw out of the cortical bone to specific dimensions. The bone screw is then inspected for structural integrity and dimensional tolerances.

It should be appreciated that while screws of cortical bone may have conformations similar to prior art screws made of metal without deviating from the teachings of the present invention, in the preferred embodiments, consideration has been given to the considerable differences in the material properties of these very different materials. Cortical bone as a material, while much stronger than cancellous bone, is profoundly weaker than the metals in common use today for the fabrication of screws such as stainless steels and titanium alloys. To that end, the preferred embodiments of the present invention have generally enlarged root diameters to increase their strength overall and to withstand the torques generated on insertion which may be further mitigated by the prior use of a tap. Further stress risers are avoided by avoiding sharp corners and unradiused edges. Further, it may be desirable to have the root diameter be generally increased nearer to the head end of the screws. The root diameter may progress from tip to head, flair beneath the head, or otherwise increase. The root diameter should ideally flow into the head rather than having a sharp step off. The thread itself should be kept strong by not unduly extending the height of the thread relative to the width of the base, or thinning the profile of the thread. The valleys between the turns of the thread are again preferably rounded rather than notched. Similarly the driver engaging area in the head portion of the screw should be kept substantial and have rounded rather than square ended slots where slots are used.

In a fourth step, the screw of cortical bone may be frozen for storage until use. Measures are provided for providing for the storability of the screws such as freezing, freeze drying.

In another, the donor is tested for communicable diseases to assure the safety of the bone. Alternatively, donor testing may be performed prior to the steps of harvesting bone from the donor.

In a sixth step, cultures are taken during the above procedure, but prior to the bone being frozen, to assure the safety of the bone.

In an alternative method of manufacturing the present invention, sterility may or may not be a goal during the manufacturing of the screw and the screw is subjected to a sterilization process including, but not limited to, exposure to radiation, freeze drying, denaturing, cleaning, chemical sterilization including the use of sterilizing liquids and/or gases.

In a further step In the manufacture of the screws of the present invention, the screw may be immersed in, or coated with, biologically active chemical agents included, but not limited to, antibiotics, or substances to pmmote bone formation such as bone morphogenetic proteins, mineralizing proteins, hydroxyapatite, or genetic material coding for the production of bone (directly or indirectly).

In a further step in the manufacturing process which may occur before or after freezing, or if not frozen then before or after sterilization the screw is packaged. In a preferred embodiment, the sterile screw is contained within a sterile container, which is itself contained within an internally sterile second container.

In a further step, each screw package comprises identifying information such as a tracking number by which the donor can be identified if need be, the identity of the manufacturer, the date of expiration by which the screw must be used, and the length and at least nominal outside diameter of the screw and if frozen the requirements for proper storage of the screw. It should be appreciated that the present invention is not limited by the specific form of the thread, and includes both machine and wood type threads. Also, the present invention does not require that the thread be fully continuous and/or of constant height. For example, where it is desirable to form a screw of the largest possible maximum outside diameter, rather than uniform outside diameter it may be desirable to then form the screw from a longitudinal diaphyseal strip selected to be wider than it is thick such that when machined the resultant screw will have a root diameter that is circular in cross section and an outside diameter that in cross section will have opposed arcuate portions, but that is incompletely circular.

It is appreciated that the present invention is not directed just to bone screws, but also to the locks themselves made of bone for locking the bone screw which may also take the form of a threaded member or even of a screw itself. The locks and bone screws of the present invention may be combined with various orthopedic and spinal plates and interbody spinal fusion implants. The implants themselves, that is the plate or the fusion implant are preferably also made of a bioresorbable material including, but not limited to, human cortical bone.

It is appreciated that bone screws of the present invention are formed along the longitudinal axis of a long bone or from a single cortex rather than being formed by cutting transversely through a long bone so as to include the opposite cortices of a long bone, that is both the near and far cortices of a tubular bone, as well as the side walls. The screws and locks of the present invention are a manufactured device that would essentially be a machined orthopedic screw, machined from a single length of cortex if of a long bone or from the thickness of an intramembraneously formed bone such as calvarium. The present invention is directed to a bone screw made substantially of cortical bone having an insertion end, a shaft at least in part threaded and a head having either a greater dimension than the outer diameter of the threaded shaft or functional means to resist the continuing forward advancement of the screw when properly utilized. By way of example, a screw made of cortical bone without a protuberant head and a thread pitch that is more tightly wound at its trailing end than at its leading end. The present invention is also specifically directed to bone screws that are not hollow through the shaft portion of the screw that are made substantially of cortical bone and which is machined and manufactured.

Moreover, the configuration of the thread of the screws is not limited to the configuration shown in the drawings but may also have any other configuration suitable for its intended purpose.

While the present invention has been described with respect to the preferred embodiments, it is appreciated that variations of the embodiments are possible without departing from the scope of the present invention.

What is claimed is:

1. A screw formed of cortical bone for use in the human body with an implant having a screw hole for receiving at least a portion of a screw therethrough, said screw comprising:
    a leading end, a trailing end apposite said leading end, and a shaft therebetween, said shaft having a mid-longitudinal axis and a length;
    a thread extending from said shaft along at least a portion of its length, said thread having an outer diameter dimensioned to pass through the screw hole in the implant;
    said trailing end being configured to cooperatively engage at least a portion of the screw hole of the implant so as to prevent said screw from linear motion along the mid-longitudinal axis of said shaft in a direction opposite to the direction of insertion when said screw is threaded through the screw hole to attach the implant to a bone portion of the human body; and
    said screw being formed substantially of cortical bone of a single cortical thickness.

2. The screw of claim 1, further comprising an enlarged portion proximate said trailing end with a dimension transverse to the mid-longitudinal axis of said shaft greater than said outer diameter of said thread, said enlarged portion configured to prevent said trailing end from passing through the screw hole in the implant.

3. The screw of claim 2, wherein said enlarged portion forms a head.

4. The screw of claim 1, wherein said trailing end includes a second thread having a different thread pitch than said thread along said shaft.

5. The screw of claim 4, wherein the thread pitch of said second thread is similar to a metal screw pitch.

6. The screw of claim 4, wherein the thread pitch of said thread along said shaft is similar to a wood screw pitch.

7. The screw of claim 1, wherein the thread pitch of said thread along said shaft is similar to a wood screw pitch.

8. The screw of claim 1, wherein at least a portion of said trailing end is expandable.

9. The screw of claim 8, wherein at least a portion of said trailing end is divided into at least two members with an opening therebetween.

10. The screw of claim 9, further comprising an insert configured to fit into said opening of said trailing end and to move said at least two members apart when inserted into said opening.

11. The screw of claim 10, wherein said insert is configured to be inserted by linear advancement into said opening.

12. The screw of claim 11, wherein said insert has a cruciate shape and said opening has a corresponding cruciate shape.

13. The screw of claim 10, wherein said insert is configured to be inserted by rotational movement into said opening.

14. The screw of claim 13, wherein said insert is threaded.

15. The screw of claim 1, wherein at feast a portion of said trailing end is configured to cooperatively engage a driving instrument for insertion of said screw.

16. The screw of claim 15, wherein said trailing end includes a recess to cooperatively engage a driving instrument.

17. The screw of claim 16, wherein said recess is one of cruciate-shape and hex-shaped.

18. The screw of claim 15, wherein said trailing end includes a protrusion to cooperatively engage a driving instrument.

19. The screw of claim 18, wherein said protrusion has a hex-shaped perimeter.

20. The screw of claim 1, wherein said thread is sharper proximate said leading end than proximate said trailing end.

21. The screw of claim 1, wherein said thread has a V-shaped cross section with an apex and a base adjacent to said shaft, said base being substantially wider than said apex.

22. The screw of claim 1, wherein said thread has a peak as measured from said shaft, the peak being greater proximate said lading end than said trailing end.

23. The screw of claim 1, wherein said shaft has a root diameter that increases in the direction from said leading end to said trailing end.

24. The screw of claim 1, wherein said leading end forms a tip and said tip is fluted.

25. The screw of claim 1, wherein said cortical bone is obtained from a human.

26. The screw of claim 1, wherein said cortical bone is obtained from a generally intramembraneously formed cortical bone.

27. The screw of claim 26, wherein said cortical bone is obtained from a human skull.

28. The screw of claim 1, wherein said cortical bone is obtained from a large tubular bone of a human.

29. The screw of claim 28, wherein said cortical bone is from the diaphyseal region of said large tubular bone.

30. The screw of claim 28, wherein the tubular bone is a femur.

31. The screw of claim 1, further comprising a bioresorbable material other than cortical bone.

32. The screw of claim 31, wherein said material includes bioresorbable plastics.

33. The screw of claim 32, wherein said material includes at least one of glycolide polymers, lactide, capralactone, trimethylene carbonate, and dioxanone.

34. The screw of claim 1, wherein said screw comprises bone growth promoting material.

35. The screw of claim 34, wherein said bone growth promoting material is selected from one of bone morphogenetic protein, hydroxyapatite, and genes coding for the production of bone.

36. The screw of claim 1, wherein said screw is treated with a bone growth promoting substance.

37. The apparatus of claim 1, in combination with a bone growth promoting material.

38. The apparatus of claim 37, wherein said bone growth promoting material includes at least one of bone morphogenetic protein, mineralizing proteins, hydroxyapatite, and genetic material coding for the production of bone.

39. A screw formed of cortical bone for use in the human body with an implant having a screw hole for receiving at least a portion of a screw therethrough, said screw comprising:
 a leading end, a trailing end opposite said leading end, and a shaft therebetween, said shaft having a mid-longitudinal axis arid a length;
 a thread extending from said shaft along at least a portion of its length, said thread having an outer diameter dimensioned to pass through the screw hole in the implant:
 said trailing end being configured to cooperatively engage at least a portion of the screw hole of the implant so as to prevent said screw from linear motion along the mid-longitudinal axis of said shaft in a direction opposite to the direction of insertion when said screw is threaded through the screw hole to attach the implant to a bone portion of the human body;
 an enlarged portion proximate said trailing end with a dimension transverse to the mid-longitudinal axis of said shaft greater than said outer diameter of said thread, said enlarged portion configured to prevent said trailing end from passing through the screw hole in the implant, said enlarged portion forming a lip; and
 said screw being formed substantially of cortical bone of a single cortical thickness.

40. The screw of claim 39, wherein said enlarged portion forms a head.

41. The screw of claim 39, wherein said trailing end includes a second thread having a different thread pitch than said thread along said shaft.

42. The screw of claim 41, wherein the thread pitch of said second thread is similar to a metal screw pitch.

43. The screw of claim 41, wherein the thread pitch of said thread along said shaft is similar to a wood screw pitch.

44. The screw of claim 39, wherein the thread pitch of said thread along said shaft is similar to a wood screw pitch.

45. The screw of claim 39, wherein at least a portion of said trailing end is expandable.

46. The screw of claim 45, wherein at least a portion of said trailing end is divided into at least two members with an opening therebetween.

47. The screw of claim 46, further comprising an insert configured to fit into said opening of said trailing end and to move said at least two members apart when inserted into said opening.

48. The screw of claim 47, wherein said insert is configured to be inserted by linear advancement into said opening.

49. The screw of claim 48, wherein said insert has a cruciate shape and said opening has a corresponding cruciate shape.

50. The screw of claim 47, wherein said insert is configured to be inserted by rotational movement into said opening.

51. The screw of claim 50, wherein said insert is threaded.

52. The screw of claim 39, wherein at least a portion of said trailing end is configured to cooperatively engage a driving instrument for insertion of said screw.

53. The screw of claim 52, wherein said trailing end includes a recess to cooperatively engage a driving instrument.

54. The screw of claim 53, wherein said recess is one of cruciate-shape and hex-shaped.

55. The screw of claim 52, wherein said trailing end includes a protrusion to cooperatively engage a driving instrument.

56. The screw of claim 55, wherein said protrusion has a hex-shaped perimeter.

57. The screw of claim 39, wherein said thread is sharper proximate said leading end than proximate said trailing end.

58. The screw of claim 39, wherein said thread has a V-shaped cross section with an apex and a base adjacent to said shaft, said base being substantially wider than said apex.

59. The screw of claim 39, wherein said thread has a peak as measured from said shaft, the peak being greater proximate said leading end than said trailing end.

60. The screw of claim 39, wherein said shaft has a root diameter that increases in the direction from said leading arid to said trailing end.

61. The screw of claim 39, wherein said leading end forms a tip and said tip is fluted.

62. The screw of claim 39, wherein said cortical bone is obtained from a human.

63. The screw of claim 39, wherein said cortical bone is obtained from a generally intramembraneously formed cortical bone.

64. The screw of claim 63, wherein said cortical bone is obtained from a human skull.

65. The screw of claim 39, wherein said conical bone is obtained from a large tubular bone of a human.

66. The screw of claim 65, wherein said cortical bone is from the diaphyseal region of said large tubular bone.

67. The screw of claim 65, wherein the tubular bone is a femur.

68. The screw of claim 39, further comprising a bioresorbable material other than cortical bone.

69. The screw of claim 68, wherein said material includes bioresorbable plastics.

70. The screw of claim 69, wherein said material includes at least one of glycolide polymers, lactide, capralactone, trimethylene carbonate, and dioxanone.

71. The screw of claim 39, wherein said screw comprises bone growth promoting material.

72. The screw of claim 71, wherein said bone growth promoting material is selected from one of bone morphogenetic protein, hydroxyapatite, and genes coding for the production of bone.

73. The screw of claim 39, wherein said screw is treated with a bone growth promoting substance.

* * * * *

UNITED STATES PATENT AND TRADEMARK OFFICE
CERTIFICATE OF CORRECTION

PATENT NO.       : 7,063,701 B2                                    Page 1 of 1
APPLICATION NO.  : 09/970241
DATED            : June 20, 2006
INVENTOR(S)      : Gary K. Michelson It is certified that error appears in the above-identified patent and that said Letters Patent is hereby corrected as shown below:

<u>Column 13, line 66</u>:
Change "apposite" to -- opposite --.

<u>Column 14, line 49</u>:
Change "feast" to -- leasts --.

<u>Column 15</u>:
Line 3: change "lading" to -- leading --; and
Line 49: change "arid" to -- and --.

<u>Column 16</u>:
Column 56: change "arid" to -- end --; and
Line 66: change "conical" to -- cortical --.

Signed and Sealed this

Third Day of October, 2006

JON W. DUDAS
*Director of the United States Patent and Trademark Office*